United States Patent
Pham et al.

(10) Patent No.: US 7,273,835 B2
(45) Date of Patent: Sep. 25, 2007

(54) AZEOTROPE-LIKE COMPOSITIONS OF DIFLUOROMETHANE

(75) Inventors: Hang T. Pham, Amherst, NY (US); Rajiv R. Singh, Getzville, NY (US); Hsueh Sung Tung, Getzville, NY (US); Franklin S. Wong, Boston, NY (US)

(73) Assignee: Honeywell International Inc., Morristown, NJ (US)

( * ) Notice: Subject to any disclaimer, the term of this patent is extended or adjusted under 35 U.S.C. 154(b) by 444 days.

(21) Appl. No.: 10/911,012

(22) Filed: Aug. 4, 2004

(65) Prior Publication Data

US 2006/0030508 A1    Feb. 9, 2006

(51) Int. Cl.
*C11D 7/50*    (2006.01)
(52) U.S. Cl. .................................... 510/177; 252/67
(58) Field of Classification Search ................ 510/177; 252/67
See application file for complete search history.

(56) References Cited

U.S. PATENT DOCUMENTS

| 5,707,497 | A | 1/1998 | Galland et al. | |
| 5,918,481 | A | 7/1999 | Pham et al. | 62/631 |
| 5,928,479 | A * | 7/1999 | Ewing et al. | 203/67 |
| 6,099,694 | A | 8/2000 | Pham et al. | 203/3 |
| 6,274,781 | B1 * | 8/2001 | Furmanek et al. | 570/168 |
| 6,458,249 | B2 * | 10/2002 | Miller et al. | 203/51 |
| 6,605,193 | B2 * | 8/2003 | Wismer | 203/57 |
| 6,635,790 | B1 | 10/2003 | Garrait et al. | |
| 2002/0001560 | A1 * | 1/2002 | Miller et al. | 423/406 |
| 2002/0157938 | A1 * | 10/2002 | Wismer | 203/50 |

FOREIGN PATENT DOCUMENTS

| EP | 0751108 A | 1/1997 |
| EP | 1253127 A | 10/2002 |
| WO | WO99/48850 A | 9/1999 |
| WO | WO 2006/017654 A2 * | 2/2006 |

* cited by examiner

*Primary Examiner*—John R. Hardee
(74) *Attorney, Agent, or Firm*—Colleen D Szuch

(57) ABSTRACT

The invention relates to azeotropic and azeotrope-like mixtures of HFC-32 and HCl or a mixture of HCl and $Cl_2$, and a process for separating the azeotrope-like mixtures.

6 Claims, No Drawings

AZEOTROPE-LIKE COMPOSITIONS OF DIFLUOROMETHANE

FIELD OF THE INVENTION

The present invention relates generally to novel compositions comprising difluoromethane.

BACKGROUND OF THE INVENTION

Many techniques are known for the production of hydrofluorocarbons (HFCs), and in particular difluoromethane (HFC-32). Certain prior methods involve fluorinating one or more chlorinated organic compounds to produce difluoromethane. The reaction product stream typically also contains byproducts and one or more unreacted starting materials. The desired difluoromethane is then recovered from the reaction product stream through one or more separation processes, such as distillation. For example, in certain difluoromethane production processes, a chlorinated organic compound, such as, for example, dichloromethane (HCC-30), and a fluorinating agent, such as, for example, hydrogen fluoride (HF), are reacted, usually after preheating, in the presence of a fluorination catalyst to generate a reaction product stream.

Distillation is well known in the art for separating the components of such reaction product streams and typically involves the use of distillation means, such as a packed column or one with trays, operated at pressures and temperatures selected to separate the reaction product stream into a stream relatively rich in the desired compound and stream relatively rich in compounds that are not desired in the finished product, such as unreacted components and unwanted byproducts. However, standard distillation techniques are generally ineffective to separate the components of azeotropic mixtures. Azeotropic binary compositions consisting of HFC-32 and chlorine are disclosed in U.S. Pat. No. 6,099,694, which is assigned to the assignee of the present invention and which is incorporated herein by reference.

The desirability of a fluorination process is generally linked to the yield and product purity resulting from the process. For example, if the desired product is the difluoromethane, the amount of such product which is recovered from the reaction product should ordinarily be as high as possible, and the type and amount of impurities contained in the final product stream should be as low as possible. While prior processes have achieved a certain level of success as measured by yield and product purity, applicants have discovered that that certain features of the prior art may raise barriers against continuing improvement of product yield and purity.

SUMMARY OF THE INVENTION

Applicants have discovered that difluoromethane and hydrogen chloride form a binary azeotrope-like composition and that difluoromethane, hydrogen chloride and chlorine form a ternary azeotrope-like composition. This discovery is particularly important because in the production of difluoromethane from chlorinated reactants, and particularly when chlorine is used as a catalyst regenerator and/or activator, difluoromethane, hydrogen chloride and chlorine are present in the reaction product. In addition to the discovery of the azeotrope-like compositions, therefore, applicants have discovered improved processes for the production of difluoromethane, including methods to eliminate or reduce the levels of hydrogen chloride and/or chlorine from the reaction product stream, and/or to recover an increased amount of hydrogen chloride and/or chlorine from the reaction product stream.

In preferred embodiments, the processes comprise reacting a chlorinated compound, preferably dichloromethane (HCC-30), with a fluorinating agent, preferably HF, to produce a product mixture comprising HFC-32 and hydrogen chloride. In certain embodiments, especially when chlorine is used as an activating agent, chlorine is also present in the reaction product stream. In one preferred embodiment of the method aspects of the present invention, one or more of the present azeotrope and azeotrope-like compositions are separated from the reaction mixture, and optionally but preferably the component parts thereof are thereafter separated to produce compositions enriched in HFC-32 and/or enriched in HCl, and/or enriched in a mixture of HCl and $Cl_2$, As used herein, the reference to enriched refers to the component having a higher concentration in the enriched composition relative to the concentration of that component in the azeotrope or azeotrope-like composition.

The azeotrope-like compositions are useful also in processes for the removal of impurities from HFC-32.

DETAILED DESCRIPTION OF PREFERRED EMBODIMENTS

The Compositions

The present compositions are azeotrope-like compositions. As used herein, the term "azeotrope-like" is intended in its broad sense to include both compositions that are strictly azeotropic and compositions that behave like azeotropic mixtures. From fundamental principles, the thermodynamic state of a fluid is defined by pressure, temperature, liquid composition, and vapor composition. An azeotropic mixture is a system of two or more components in which the liquid composition and vapor composition are equal at the state pressure and temperature. In practice, this means that the components of an azeotropic mixture are constant boiling and cannot be separated during distillation.

As the term is used herein, "azeotrope-like" compositions behave like azeotropic mixtures, that is, they are constant boiling or essentially constant boiling. In other words, for azeotrope-like compositions, the composition of the vapor formed during boiling or evaporation is identical, or substantially identical, to the original liquid composition. Thus, with boiling or evaporation, the liquid composition changes, if at all, only to a minimal or negligible extent. This is to be contrasted with non-azeotrope-like compositions in which, during boiling or evaporation, the liquid composition changes to a substantial degree. All azeotrope-like compositions of the invention within the indicated ranges as well as certain compositions outside these ranges are azeotrope-like.

The azeotrope-like compositions of the invention may include additional components that do not form new azeotropic or azeotrope-like systems, or additional components that are not in the first distillation cut. The first distillation cut is the first cut taken after the distillation column displays steady state operation under total reflux conditions. One way to determine whether the addition of a component forms a new azeotropic or azeotrope-like system so as to be outside of this invention is to distill a sample of the composition with the component under conditions that would be expected to separate a non-azeotropic mixture into its separate components. If the mixture containing the additional component is non-azeotropic or non-azeotrope-like, the additional component will fractionate from the azeotropic or azeotrope-like components. If the mixture is azeotrope-like, some finite amount of a first distillation cut will be obtained that contains all of the mixture components that is constant boiling or behaves as a single substance.

It follows from this that another characteristic of azeotrope-like compositions is that there is a range of compositions containing the same components in varying proportions that are azeotrope-like or constant boiling. All such compositions are intended to be covered by the terms "azeotrope-like" and "constant boiling". As an example, it is well known that at differing pressures, the composition of a given azeotrope will vary at least slightly, as does the boiling point of the composition. Thus, an azeotrope of A and B represents a unique type of relationship, but with a variable composition depending on temperature and/or pressure. It follows that, for azeotrope-like compositions, there is a range of compositions containing the same components in varying proportions that are azeotrope-like. All such compositions are intended to be covered by the term azeotrope-like as used herein.

Difluoromethane/HCl/Cl$_2$

One embodiment of the invention provides azeotrope-like compositions comprising difluoromethane, hydrogen chloride and chlorine. Preferably, the novel azeotrope-like compositions of this embodiment comprise effective amounts of the HFC-32, hydrogen chloride and chlorine. The term "effective amounts" as used herein means the amount of each component which upon combination with the other component or components, results in the formation of the present azeotrope-like compositions.

These embodiments preferably provide azeotrope-like compositions comprising, and preferably consisting essentially of, from about 1 to about 20 parts by weight HFC-32, from about 70 to about 99.9 parts by weight of hydrogen chloride, and from about 1 to about 13 parts by weight chlorine. Such compositions are preferably characterized by a substantially constant vapor pressures of about 45±3 psia, more preferably about 45±2 psia, and even more preferably about 45 psia at a temperature of about 59° C.

The preferred, more preferred, and most preferred compositions of this embodiment are set forth in Table 1. The numerical ranges in Table 1 are to be understood to be prefaced by the term "about".

TABLE 1

| Components | Preferred (pbw) | More Preferred (pbw) | Most Preferred (pbw) |
| --- | --- | --- | --- |
| HFC-32 | 0.25-20 | 0.25-15 | 0.25-10 |
| HCl | 70-99.5 | 80-99.5 | 95-99.5 |
| Cl$_2$ | 0.25-13 | 0.25-5 | 0.25-3 |

Difluoromethane and Hydrogen Chloride

One embodiment of the invention provides azeotrope-like compositions comprising, and preferably consisting essentially of, difluoromethane and hydrogen chloride. Preferably, the novel azeotrope-like compositions of this embodiment comprise effective amounts of difluoromethane and hydrogen chloride. Such compositions preferably comprise, and even more preferably consist essentially of, from about 1 to about 20 parts by weight HFC-32, and from about 80 to about 99 parts by weight of HCl. In many embodiments, such preferred compositions are characterized by a substantially constant vapor pressure of about 50±4 psia, more preferably about 50±2 psia, and even more preferably about 50 psia at a temperature of about −59.3° C.

The preferred, more preferred, and most preferred compositions of this embodiment are set forth in Table 2A. The numerical ranges in Table 2A are to be understood to be prefaced by the term "about".

TABLE 2A

| Components | Preferred (pbw) | More Preferred (pbw) | Most Preferred (pbw) |
| --- | --- | --- | --- |
| HFC-32 | 1-20 | 1-10 | 1-5 |
| HCl | 80-99 | 90-99 | 95-99 |

The following Table 2B provides vapor pressure data for the HFC-32/HCl compositions according to preferred embodiments of the present invention.

TABLE 2B

| HFC-32/HCl Azeotrope | |
| --- | --- |
| HFC-32/HCl Wt Ratios | Vapor Pressure (psia) at −59.2° C. |
| 100/0 | 53.6 |
| 97.7/2.3 | 53.1 |
| 88.9/11.1 | 50.6 |
| 84.0/16 | 48.9 |
| 80.3/19.7 | 48.0 |

The Methods

Fluorination Processes

In one embodiment, the method aspects of the present invention include improved fluorination processes comprising the steps of (a) reacting one or more reactants to produce a reaction product comprising at least HFC-32 and HCl, removing from said reaction product an azeotrope-like composition comprising HFC-32 and HCl. Optionally, but preferably, the methods also include separating at least a portion of the HCl from said removed azeotrope or azeotrope-like HFC-32/HCl composition to produce a composition enriched in HFC-32. Optionally, but preferably, the methods may also include producing from said azeotrope or azeotrope-like composition a composition enriched in HCl.

In another embodiment, the method aspects of the present invention include improved fluorination processes comprising the steps of (a) reacting one or more reactants to produce a reaction product comprising at least HFC-32, HCl and Cl$_2$, removing from said reaction product an azeotrope or azeotrope-like composition comprising HFC-32, HCl and Cl$_2$. Optionally, but preferably, the methods also include separating at least a portion of the HCl and/or the Cl$_2$ from said removed azeotrope or azeotrope-like HFC-32/HCl/Cl$_2$ composition to produce a composition enriched in HFC-32. The term "enriched" is used herein to refer to the condition during the distillation of a mixture in which the concentration of one component in either the distillate or a bottoms product is higher relative to its concentration in the mixture.

Optionally, but preferably, the methods may also include producing from said azeotrope or azeotrope-like composition a composition enriched in Cl$_2$. When one or more of the optional separations step is used, it is generally preferred that at least a portion of the Cl$_2$ so separated is recycled to the chlorination reaction.

The fluorination step of the present invention can be carried out in accordance with any process known in the art, and particulars of all such processes are within the scope of the present invention and need not be explained in detail here. In is sufficient to note that the present processes generally a mixture of halogenated compounds, including HFC-32, HCl and other byproducts, including in certain embodiments $Cl_2$. Thus, the mixture of reactants, byproducts and reaction intermediates of the process may be present along with the HCl, $Cl_2$ and HFC-32 in the mixture.

Accordingly, in one embodiment, the present invention provides a process for separating HFC-32 from an HFC-32/$HCl_2$ azeotrope-like mixture. In other embodiments, the present invention provides a process for separating HFC-32 from an HFC-32/HCl/$Cl_2$ azeotropic or azeotrope-like mixture. It will be appreciated by those skilled in the art that several techniques are know and available for separating azeotropic or azeotrope-like compositions into compositions enriched in one or more of the components thereof. For example, liquid-liquid phase separation techniques are generally effective in this regard and are believed to adaptable for use in accordance with the present invention. In other embodiments, the present process comprises, consists essentially of, or consists of the steps of:

(A) distilling a mixture comprising HFC-32 and HCl, or HFC-32 and a mixture of HCl and $Cl_2$, at a first pressure to produce a stream consisting of an azeotrope-like composition of the present invention; and (B) distilling said azeotrope-like composition of the present invention at a second pressure to produce a stream enriched in any one of HFC-32, HCl and $Cl_2$. The distillation steps of the present methods may be performed using a single distillation column or a series of distillation columns. In embodiments wherein a single distillation column is used, the methods of the present invention are typically performed as batch distillations. The mixture may be fed, for example, into a batch distillation column operating at a first pressure. The azeotrope like composition of the present invention is then collected and refed into the column at a second pressure. Preferably, the methods of the present invention are performed using a series of distillation columns, meaning at least two columns, operating at different pressures in a batch or continuous distillation. Examples of distillation columns and methods suitable for use in the present invention are disclosed in U.S. Pat. No. 5,918,481 (issued to AlliedSignal), which is incorporated herein by reference.

Whether the distillation process is continuous or batch, the pressures at which the distillations are conducted preferably are such that conventional distillation apparatus can be used. The higher distillation pressure generally may range from about 40 to about 400 psia, preferably from about 60 to about 200 psia. The lower distillation pressure generally may range from about 10 psia to about 40 psia, preferably from about 15 psia to less than about 30 psia.

The temperatures at which these distillations are performed are directly related to the boiling points and pressures used, and are well within the scope of knowledge of one skilled in the art in view of the teachings contained herein.

In certain other embodiments, the present invention provides a method for removing HFC-32 from a mixture containing HFC-32 and at least one impurity. As used herein, the term "impurity" refers to any compound present in a mixture with HFC-32 from which it is desirable, for a given application, to separate the HFC-32. Preferably, the impurity itself does not form an azeotrope-like mixture with HFC-32, HCl, $Cl_2$ or a mixture of HCl and $Cl_2$. Typical impurities include other halocarbons which may be miscible with HFC-32 such as, for example, chlorofluoromethane (HCFC-31) or dichloromethane (HCC-30).

The method for separating HFC-32 and at least an impurity preferably comprises adding HCl or a mixture of HCl and $Cl_2$ to the mixture in an amount sufficient to form an azeotrope-like composition of the HFC-32 and the HCl or a mixture of HCl and $Cl_2$, and then separating the azeotrope-like composition from the mixture.

The azeotropic composition of the present invention may be separated from the mixture comprising the impurity by any of a number of conventional methods. Examples of separation methods include, for example, distillation, scrubbing, other art-recognized separating means, and combinations of two or more thereof. Any mixture containing HFC-32 and at least one impurity may be used in the present method. While such mixtures may be provided via any conventional source, in certain preferred embodiments, the mixtures are reaction products resulting from a manufacturing process, most notably, the production of HFC-32.

Those of skill in the art will recognize that the amount of HCl or a mixture of HCl and $Cl_2$ to be added to the mixture, and to form an azeotrope-like composition, will depend on the conditions under which the azeotrope-like composition is formed. In light of the disclosure herein, those of skill in the art will be readily able to determine the amounts of HCl or a mixture of HCl and $Cl_2$ necessary to form azeotrope-like compositions with HFC-32 under a wide range of pressures and temperatures.

EXAMPLES

The following non-limiting examples serve to illustrate the invention.

Example 1

Binary compositions consisting essentially of HFC-32 and HCl are blended to form homogeneous mixtures having different compositions. The vapor pressures of the mixtures were measured at −59.2° C.

Table 2b above shows the vapor pressure measurement of HFC-32/HCl as a function of composition at a substantially constant temperature of −52.9° C. From this data it is observed that at −59.2° C. the composition exhibits azeotrope-like properties from about 1 to about 20 weight percent HFC-32. Based on further observations made during the experiment, it is determined that the composition at which the vapor pressure is the maximum is from greater than 0 up to about 2.3 weight percent HFC-32 at −59.2° C.

Example 2

Binary compositions consisting essentially of HFC-32, $Cl_2$ and HCl are blended to form homogeneous mixtures having different compositions. The vapor pressures of the mixtures were measured at −59.2° C. Table 3 shows the vapor pressure measurement of HFC-32/HCl/$Cl_2$ as a function of composition at a constant temperature of −59.2° C. From this data it is observed that at −59.2° C. the composition exhibits azeotrope-like properties at compositions comprising from about 17 to about 20 weight percent HFC-32 and from about 1 to about 13 weight percent C12, the balance being HCl.

TABLE 3

| WEIGHT PERCENT (remainder HFC-32) | | VAPOR PRESSURE (PSIA) |
|---|---|---|
| HFC-32 | CL$_2$ | AT −59.2° C. |
| 19.4 | 1.5 | 46.3 |
| 18.3 | 6.9 | 45.2 |
| 17.2 | 12.3 | 43.8 |

What is claimed is:

1. An azeotrope-like composition, which consists essentially of difluoromethane (HFC-32) and HCl.

2. The composition of claim 1 having a vapor pressure of from about 45 psia to about 55 psia at a temperature of about −59.3° C.

3. The composition of claim 2 consisting essentially of from about 1 to about 20 weight percent HFC-32 and from about 80 to about 99 weight percent HCl.

4. The composition of claim 2, which consists essentially of from about 1 to about 10 weight percent HFC-32 and from about 90 to about 99 weight percent HCl.

5. The composition of claim 2, which consists essentially of from about 1 weight percent to about 5 weight percent HFC-32 and from about 95 to about 99 weight percent HCl.

6. A method of forming an azeotropic or azeotrope-like composition which consists essentially of combining from about from about 1 to about 20 weight percent HFC-32 and from about 80 to about 99 weight percent HCl, which composition has a vapor pressure of from about 45 psia to about 55 psia at temperature of about −59° C.

* * * * *